United States Patent
Lee

(10) Patent No.: US 8,673,374 B1
(45) Date of Patent: Mar. 18, 2014

(54) COMPOSITE ESSENTIAL OIL FOR EXPANDING CORPUS CAVERNOSUM

(71) Applicant: Tien-Te Lee, Shanghai (CN)

(72) Inventor: Tien-Te Lee, Shanghai (CN)

(*) Notice: Subject to any disclaimer, the term of this patent is extended or adjusted under 35 U.S.C. 154(b) by 0 days.

(21) Appl. No.: 13/687,926

(22) Filed: Nov. 28, 2012

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2012/0288468 A1* 11/2012 Wang et al. .................. 424/76.6

* cited by examiner

*Primary Examiner* — Michael Meller
(74) *Attorney, Agent, or Firm* — Muncy, Geissler, Olds & Lowe, P.C.

(57) ABSTRACT

A composite essential oil for expanding corpus cavernosum is composed of 30~50 parts of a cinnamon essential oil, 20~40 parts of a black pepper essential oil, 40~60 parts of a juniper essential oil, 20-40 parts of a ginger essential oil, 0~30 parts of a jasmine essential oil and 0-20 parts of a clove essential oil by volume and provided for overcoming a men's health problem, particularly the erectile dysfunction.

1 Claim, No Drawings

COMPOSITE ESSENTIAL OIL FOR EXPANDING CORPUS CAVERNOSUM

FIELD OF THE INVENTION

The present invention relates to an essential oil, and more specifically to a composite essential oil for expanding corpus cavernosum.

BACKGROUND OF THE INVENTION

In modern societies, men have much greater pressure on work, family and life than women, and most middle-aged men get all kinds of sickness easily, so that the issue of men's health is highly anticipated. According unofficial statistics, China has about 660 million men especially middle-aged and elderly men are troubled by male diseases which affect their physical and mental health and quality of life. The diseases of male reproductive systems are more serious than those of female's, but most of the time, men endure the trouble of male diseases silently since they worry about the problems of their diseases being known to others, affecting their image and losing face. The male diseases not just seriously affect men's health only, but also affect a couple's marital relation and family harmony.

Due to the daily work and living pressure, many middle-aged men or men of early-thirty are suffered by erectile dysfunction. According to statistics, almost half of the middle-aged and elderly men (over 40 years old) have the problem of erectile dysfunction which affects a couple's normal life and passion communication seriously or even ruins a family. The erectile dysfunction is usually a premonitory symptom of common chronic diseases such as diabetes, hypertension and coronary heart disease, and thus it is necessary to attach great importance to the issue of erectile dysfunction in order to prevent more serious disorders.

At present, infertility has become a "common problem" in China. In past five years, millions of couples have sought medical treatment each year due to infertility. Surveys show that one out of every ten couples has the infertility problem. In recent 20 years, the number of infertile patients is doubled in China, and azoospermia, oligospermia, weak sperm, dead sperm and other conditions have increased significantly. Compared with the conditions three to four decades ago, the number of sperms per milliliter is dropped significantly from 100 millions to 20~40 millions now. What are the causes of infertility? Factors including environmental pollution, unhealthy habits, radiation and particularly the surge of work pressure have substantial impacts on men's fertility.

SUMMARY OF THE INVENTION

In view of the aforementioned problems, it is a primary objective of the present invention to overcome the problems of the prior art by providing a composite essential oil for expanding corpus cavernosum.

To achieve the foregoing objective, the present invention provides a composite essential oil for expanding corpus cavernosum, comprising any three of the following composition with a specific volume proportion: 30~50 parts of a cinnamon essential oil; 20~40 parts of a black pepper essential oil; 40~60 parts of a juniper essential oil; 20~40 parts of a ginger essential oil; and 20~40 parts of a jasmine essential oil.

The composite essential oil further comprises 0~20 parts of a clove essential oil.

The composite essential oil further comprises 30~60 parts of a base oil.

The base oil is a grape seed oil.

The base oil has a volume proportion of 50 parts.

The present invention has the advantage of overcoming many men's health problems, particularly the male erectile dysfunction.

DESCRIPTION OF THE PREFERRED EMBODIMENTS

The technical characteristics of the present invention will become apparent with the detailed description of the preferred embodiments as follows.

The juniper essential oil can assist diuresis, induction of menstruation, detoxification, midwifery, anti-bacterial effect, sweating, and purification and improve oily congestive skin, scalp sebum, acne, blocked pores, dermatitis, eczema, and psoriasis. The juniper essential oil can assist liver detoxification, liver function, indigestion, nausea, vomiting, flatulence, excess uric acid, kidney detoxification, kidney stones, diuretic, antibacterial effect of urinary tract, hemorrhoids, prostate gland, arthritis, rheumatism, baldness, oily skin, wrinkle removal, pigment decomposition, anti-plaque, anti-cellulitis, acne, weight loss, scar, eczema, ringworm, sciatica, menstrual disorder, amenorrhea, production, emotion activation, and physical and mental relief of pressure, aphrodisiac, supplement, energy, disinfection, sterilization, and detoxification.

The black pepper essential oil is extracted by mixing and shaking a piper nigrum plant, and this essential oil is a piper nigrum oil extracted from immature red fruits and obtained by mixing and shaking the fruit, and the white pepper essential oil is also obtained from the same fruit by the same method, except that the fruit is fully mature, and the epicarp of the fruit is removed before its drying under the sun. This mild spicy essential oil facilitates increasing our body temperature, cheering up our spirit, relieving muscle and joint pains, and improving immunity and digestive system and kidney function, and promoting cutaneous circulation to eliminate bruises on skin. The black pepper essential oil is composed of p. orientalis, ketone, pinene, camphene, sabinene, phellandrene, myrcene, limonene, caryophyllene (terpene), farnesene or farnesene red (sweet) myrrh (terpenes), linalool, terpinene, and the black pepper essential oil can help pain relief, rheumatism, chill, flu, cold, and the promotion of blood circulation, exhaustion, muscle pain, physical and emotional coldness, neurotoxic and fever. In addition, it can promote the secretion of saliva, increase appetite, promote gastrointestinal motility, condition colon muscle and is the black pepper essential oil is a common tonic used to help digestion, and it also has the effects of medical treatment, sterilization, antispasmodic, anti-toxin and the effects of stimulating libido, promotion, sweating, digestion, diuretic effect, antipyretic, relaxation, redness elimination and tonic effect (especially for spleen).

The ginger essential oil can be used for treating bone fracture, rheumatic disease, arthritis, bruises, carbuncles, nausea, hangover, excursions and boat vomiting, colds and flu, catarrh, congestion, cough, sinusitis, skin pain, sore throat, diarrhea, hernia, cramps, chills and fever. The ginger essential oil has a spicy smell like lemon and pepper. The ginger essential oil is chemically composed of pinene, camphene, cineole, linalool, borneol, dilute spirit or terpinene, orange alcohol, neral, geraniol, geranial, geranyl acetate, red [sweet] myrrh (terpenes) and gingerene. The main effects of ginger essential oil include aphrodisiac, flatulence, phlegm, fever, laxative, warming and activating human body, calming stomach, promoting sweating, and tonic. The ginger essential oil can be used for the treatment of bone fracture, rheumatic disease, arthritis, bruising, carbuncle, nausea, hangover, travel and boat vomiting, cold and flu, catarrh, congestion, cough, sinusitis, skin pain, sore throat, diarrhea, hernia, cramp, chill and fever. It also helps dissipating blood stasis, governance trauma, conditioning oily skin and pale skin. However, the ginger essential oil is not suitable for use in facial skin care. It can adjust the shampooed hair in a shampoo and cure headache.

The jasmine essential oil is called the "King of Essential Oil" since it has the effects of aphrodisiac, regulating reproductive systems, promoting lactation, conditioning dry and sensitive skin, fading marks and scars, and enhancing skin elasticity.

The cinnamon essential oil has a mild skin convergence effect, and the effects of tightening loosened tissues and removing warts. The cinnamon essential oil can further resist skin ageing, promote blood circulation and provide a convergence effect. It is noteworthy that the cinnamon essential oil is a medical botanic essential oil with moderate irritation.

The clove essential oil is extracted from a myrtaceae syzygium clove and capable for treating toothache, bronchitis, neuralgia, gastric acid, anti-respiratory system and urinary tract infection, relieving discomfort and pain caused by dysentery, improving weak physique and anemia, aphrodisiac (impotence and frigidity), deworming, promoting blood circulation, treatment of skinulcers and wound infection, and treatment of scabies, and enhancing rough skin.

Preferred Embodiment 1

Mix and shake 30 parts of cinnamon essential oil, 22 parts of black pepper essential oil, 40 parts of juniper essential oil and 21 parts of ginger essential oil uniformly, and then fill the mixed oil into a sealed bottle.

Preferred Embodiment 2

Mix and shake 50 parts of cinnamon essential oil, 39 parts of black pepper essential oil, 58 parts of juniper essential oil and 38 parts of ginger essential oil uniformly, and then fill the mixed oil into a sealed bottle.

Preferred Embodiment 3

Mix and shake 45 parts of cinnamon essential oil, 32 parts of black pepper essential oil, 51 parts of juniper essential oil and 32 parts of ginger essential oil uniformly, and then fill the mixed oil into a sealed bottle.

Preferred Embodiment 4

Mix and shake 32 parts of cinnamon essential oil, 21 parts of black pepper essential oil, 42 parts of juniper essential oil, 23 parts of ginger essential oil and 29 parts of jasmine essential oil uniformly, and then fill the mixed oil into a sealed bottle.

Preferred Embodiment 5

Mix and shake 49 parts of cinnamon essential oil, 39 parts of black pepper essential oil, 58 parts of juniper essential oil, 38 parts of ginger essential oil, 25 parts of jasmine essential oil and 19 parts of clove essential oil uniformly, and then fill the mixed oil into a sealed bottle.

Preferred Embodiment 6

Mix and shake 40 parts of cinnamon essential oil, 30 parts of black pepper essential oil, 50 parts of juniper essential oil, 30 parts of ginger essential oil, 20 parts of jasmine essential oil, 20 parts of clove essential oil and 50 parts of grape seed oil uniformly, and then fill the mixed oil into a sealed bottle.

Preferred Embodiment 7

Mix and shake 50 parts of cinnamon essential oil, 39 parts of black pepper essential oil, 58 parts of juniper essential oil, 38 parts of ginger essential oil, 50 parts of grape seed oil uniformly, and then fill the mixed oil into a sealed bottle.

Preferred Embodiment 8

Mix and shake 45 parts of cinnamon essential oil, 32 parts of black pepper essential oil and 33 parts of juniper essential oil uniformly, and then fill the mixed oil into a sealed bottle.

Preferred Embodiment 9

Mix and shake 32 parts of cinnamon essential oil, 58 parts of juniper essential oil and 38 parts of ginger essential oil uniformly, and then fill the mixed oil into a sealed bottle.

Preferred Embodiment 10

Mix and shake 48 parts of cinnamon essential oil, 32 parts of black pepper essential oil and 30 parts of ginger essential oil uniformly, and then fill the mixed oil into a sealed bottle.

Preferred Embodiment 11

Mix and shake 39 parts of cinnamon essential oil, 25 parts of black pepper essential oil and 38 parts of jasmine essential oil uniformly, and then fill the mixed oil into a sealed bottle.

Preferred Embodiment 12

Mix and shake 46 parts of cinnamon essential oil, 58 parts of juniper essential oil and 39 parts of ginger essential oil uniformly, and then fill the mixed oil into a sealed bottle.

Preferred Embodiment 13

Mix and shake 40 parts of cinnamon essential oil, 48 parts of juniper essential oil and 23 parts of jasmine essential oil uniformly, and then fill the mixed oil into a sealed bottle.

Preferred Embodiment 14

Mix and shake 45 parts of cinnamon essential oil, 35 parts of ginger essential oil and 33 parts of jasmine essential oil uniformly, and then fill the mixed oil into a sealed bottle.

Preferred Embodiment 15

Mix and shake 20 parts of black pepper essential oil, 55 parts of juniper essential oil and 38 parts of ginger essential oil uniformly, and then fill the mixed oil into a sealed bottle.

Preferred Embodiment 16

Mix and shake cinnamon essential oil 31 parts; black pepper essential oil 22 parts; juniper essential oil 40 parts uniformly, and then fill the mixed oil into a sealed bottle.

Preferred Embodiment 17

Mix and shake 50 parts of cinnamon essential oil, 38 parts of black pepper essential oil and 60 parts of juniper essential oil uniformly, and then fill the mixed oil into a sealed bottle.

Preferred Embodiment 18

Mix and shake 42 parts of cinnamon essential oil, 33 parts of black pepper essential oil and 52 parts of juniper essential oil uniformly, and then fill the mixed oil into a sealed bottle.

Preferred Embodiment 19

Mix and shake 30 parts of cinnamon essential oil, 21 parts of black pepper essential oil and 20 parts of ginger essential oil uniformly, and then fill the mixed oil into a sealed bottle.

Preferred Embodiment 20

Mix and shake 48 parts of cinnamon essential oil, 37 parts of black pepper essential oil and 40 parts of ginger essential oil uniformly, and then fill the mixed oil into a sealed bottle.

Preferred Embodiment 21

Mix and shake 45 parts of cinnamon essential oil, 35 parts of black pepper essential oil and 55 parts of ginger essential oil uniformly, and then fill the mixed oil into a sealed bottle.

Preferred Embodiment 22

Mix and shake 31 parts of cinnamon essential oil, 20 parts of black pepper essential oil and 21 parts of jasmine essential oil uniformly, and then fill the mixed oil into a sealed bottle.

Preferred Embodiment 23

Mix and shake 49 parts of cinnamon essential oil, 40 parts of black pepper essential oil and 40 parts of jasmine essential oil uniformly, and then fill the mixed oil into a sealed bottle.

Preferred Embodiment 24

Mix and shake 42 parts of cinnamon essential oil, 29 parts of black pepper essential oil and 31 parts of jasmine essential oil uniformly, and then fill the mixed oil into a sealed bottle.

Preferred Embodiment 25

Mix and shake 20 parts of black pepper essential oil, 43 parts of juniper essential oil and 20 parts of ginger essential oil uniformly, and then fill the mixed oil into a sealed bottle.

Preferred Embodiment 26

Mix and shake 37 parts of black pepper essential oil, 58 parts of juniper essential oil and 40 parts of ginger essential oil uniformly, and then fill the mixed oil into a sealed bottle.

Preferred Embodiment 27

Mix and shake 29 parts of black pepper essential oil, 51 parts of juniper essential oil and 31 parts of ginger essential oil uniformly, and then fill the mixed oil into a sealed bottle.

Preferred Embodiment 28

Mix and shake 21 parts black pepper essential oil, 42 parts of juniper essential oil and 22 parts of jasmine essential oil uniformly, and then fill the mixed oil into a sealed bottle.

Preferred Embodiment 29

Mix and shake 35 parts of black pepper essential oil, 57 parts of juniper essential oil and 37 parts of jasmine essential oil uniformly, and then fill the mixed oil into a sealed bottle.

Preferred Embodiment 30

Mix and shake 31 parts of black pepper essential oil, 52 parts of juniper essential oil and 31 parts of jasmine essential oil uniformly, and then fill the mixed oil into a sealed bottle.

Preferred Embodiment 31

Mix and shake 22 parts of ginger essential oil, 42 parts of juniper essential oil and 22 parts of jasmine essential oil uniformly, and then fill the mixed oil into a sealed bottle.

Preferred Embodiment 32

Mix and shake 33 parts of ginger essential oil, 57 parts of juniper essential oil and 37 parts of jasmine essential oil uniformly, and then fill the mixed oil into a sealed bottle.

Preferred Embodiment 33

Mix and shake 32 parts of ginger essential oil, 52 parts of juniper essential oil and 31 parts of jasmine essential oil uniformly, and then fill the mixed oil into a sealed bottle.

Preferred Embodiment 34

Mix and shake 30 parts of cinnamon essential oil, 22 parts of black pepper essential oil, 40 parts of juniper essential oil and 21 parts of ginger essential oil uniformly, and then fill the mixed oil into a sealed bottle.

Preferred Embodiment 35

Mix and shake 50 parts of cinnamon essential oil, 38 parts of black pepper essential oil, 59 parts of juniper essential oil and 38 parts of ginger essential oil uniformly, and then fill the mixed oil into a sealed bottle.

Preferred Embodiment 36

Mix and shake 41 parts of cinnamon essential oil, 32 parts of black pepper essential oil, 51 parts of juniper essential oil and 31 parts of ginger essential oil uniformly, and then fill the mixed oil into a sealed bottle.

Preferred Embodiment 37

Mix and shake 30 parts of cinnamon essential oil, 22 parts of black pepper essential oil, 40 parts of juniper essential oil and 21 parts of ginger essential oil uniformly, and then fill the mixed oil into a sealed bottle.

Preferred Embodiment 38

Mix and shake 50 parts of cinnamon essential oil, 38 parts of black pepper essential oil, 59 parts of juniper essential oil and 38 parts of ginger essential oil uniformly, and then fill the mixed oil into a sealed bottle.

Preferred Embodiment 39

Mix and shake 32 parts of cinnamon essential oil, 32 parts of black pepper essential oil, 51 parts of juniper essential oil and 31 parts of ginger essential oil uniformly, and then fill the mixed oil into a sealed bottle.

Preferred Embodiment 40

Mix and shake 20 parts of ginger essential oil, 21 parts of black pepper essential oil, 39 parts of juniper essential oil and 21 parts of jasmine essential oil uniformly, and then fill the mixed oil into a sealed bottle.

Preferred Embodiment 41

Mix and shake 40 parts of ginger essential oil, 39 parts of black pepper essential oil, 60 parts of juniper essential oil and 37 parts of jasmine essential oil uniformly, and then fill the mixed oil into a sealed bottle.

Preferred Embodiment 42

Mix and shake 31 parts of ginger essential oil, 31 parts of black pepper essential oil, 50 parts of juniper essential oil and 32 parts of jasmine essential oil uniformly, and then fill the mixed oil into a sealed bottle.

Preferred Embodiment 43

Mix and shake 31 parts of cinnamon essential oil, 22 parts of ginger essential oil, 20 parts of black pepper essential oil, 43 parts of juniper essential oil and 22 parts of jasmine essential oil uniformly, and then fill the mixed oil into a sealed bottle.

Preferred Embodiment 44

Mix and shake 49 parts of cinnamon essential oil, 38 parts of ginger essential oil, 40 parts of black pepper essential oil, 59 parts of juniper essential oil and 38 parts of jasmine essential oil uniformly, and then fill the mixed oil into a sealed bottle.

Preferred Embodiment 45

Mix and shake 42 parts of cinnamon essential oil, 32 parts of ginger essential oil, 33 parts of black pepper essential oil, 33 parts of juniper essential oil and 35 parts of jasmine essential oil uniformly, and then fill the mixed oil into a sealed bottle.

Preferred Embodiment 46

Mix and shake 31 parts of cinnamon essential oil, 22 parts of black pepper essential oil, 40 parts of juniper essential oil and 1 part of clove essential oil uniformly, and then fill the mixed oil into a sealed bottle.

Preferred Embodiment 47

Mix and shake 49 parts of cinnamon essential oil, 38 parts of black pepper essential oil, 60 parts of juniper essential oil and 19 parts of clove essential oil uniformly, and then fill the mixed oil into a sealed bottle.

Preferred Embodiment 48

Mix and shake 42 parts of cinnamon essential oil, 33 parts of black pepper essential oil, 52 parts of juniper essential oil and 11 parts of clove essential oil uniformly, and then fill the mixed oil into a sealed bottle.

Preferred Embodiment 49

Mix and shake 32 parts of cinnamon essential oil, 21 parts of black pepper essential, 20 parts of oil ginger essential oil and 1 part of clove essential oil uniformly, and then fill the mixed oil into a sealed bottle.

Preferred Embodiment 50

Mix and shake 48 parts of cinnamon essential oil, 37 parts of black pepper essential oil, 40 parts of ginger essential oil and 18 parts of clove essential oil uniformly, and then fill the mixed oil into a sealed bottle.

Preferred Embodiment 51

Mix and shake 45 parts of cinnamon essential oil, 35 parts of black pepper essential oil, 55 parts of ginger essential oil and 10 parts of clove essential oil uniformly, and then fill the mixed oil into a sealed bottle.

Preferred Embodiment 52

Mix and shake 31 parts of cinnamon essential oil, 32 parts of black pepper essential oil, 21 parts of jasmine essential oil and 2 parts of clove essential oil uniformly, and then fill the mixed oil into a sealed bottle.

Preferred Embodiment 53

Mix and shake cinnamon essential oil 49 parts; black pepper essential oil 39 parts; jasmine essential oil 38 parts; clove essential oil 18 parts uniformly, and then fill the mixed oil into a sealed bottle.

Preferred Embodiment 54

Mix and shake 42 parts of cinnamon essential oil, 29 parts of black pepper essential oil, 31 parts of jasmine essential oil and 10 parts of clove essential oil uniformly, and then fill the mixed oil into a sealed bottle.

Preferred Embodiment 55

Mix and shake 20 parts of black pepper essential oil, 40 parts of juniper essential oil, 20 parts of ginger essential oil and 3 parts of clove essential oil uniformly, and then fill the mixed oil into a sealed bottle.

Preferred Embodiment 56

Mix and shake 40 parts of black pepper essential oil, 60 parts of juniper essential oil, 40 parts of ginger essential oil and 20 parts of clove essential oil uniformly, and then fill the mixed oil into a sealed bottle.

Preferred Embodiment 57

Mix and shake 29 parts of black pepper essential oil, 51 parts of juniper essential oil, 31 parts of ginger essential oil and 9 parts of clove essential oil uniformly, and then fill the mixed oil into a sealed bottle.

Preferred Embodiment 58

Mix and shake 21 parts of black pepper essential oil, 42 parts of juniper essential oil, 22 parts of jasmine essential oil and 3 parts of clove essential oil uniformly, and then fill the mixed oil into a sealed bottle.

Preferred Embodiment 59

Mix and shake 35 parts of black pepper essential oil, 57 parts of juniper essential oil, 37 parts of jasmine essential oil and 20 parts of clove essential oil uniformly, and then fill the mixed oil into a sealed bottle.

Preferred Embodiment 60

Mix and shake 31 parts of black pepper essential oil, 52 parts of juniper essential oil, 31 parts of jasmine essential oil and 11 parts of clove essential oil uniformly, and then fill the mixed oil into a sealed bottle.

Preferred Embodiment 61

Mix and shake 22 parts of ginger essential oil, 42 parts of juniper essential oil, 22 parts of jasmine essential oil and 3 parts of clove essential oil uniformly, and then fill the mixed oil into a sealed bottle.

Preferred Embodiment 62

Mix and shake 33 parts of ginger essential oil, 57 parts of juniper essential oil, 37 parts of jasmine essential oil and 18 parts of clove essential oil uniformly, and then fill the mixed oil into a sealed bottle.

Preferred Embodiment 63

Mix and shake 32 parts of ginger essential oil, 52 parts of juniper essential oil, 31 parts of jasmine essential oil and 12 parts of clove essential oil uniformly, and then fill the mixed oil into a sealed bottle.

Preferred Embodiment 64

Mix and shake 30 parts of cinnamon essential oil, 22 parts of black pepper essential oil, 40 parts of juniper essential oil, 21 parts of ginger essential oil and 2 parts of clove essential oil uniformly, and then fill the mixed oil into a sealed bottle.

Preferred Embodiment 65

Mix and shake 50 parts of cinnamon essential oil, 40 parts of black pepper essential oil, 59 parts of juniper essential oil, 38 parts of ginger essential oil and 19 parts of clove essential oil uniformly, and then fill the mixed oil into a sealed bottle.

Preferred Embodiment 66

Mix and shake 40 parts of cinnamon essential oil, 32 parts of black pepper essential oil, 51 parts of juniper essential oil, 31 parts of ginger essential oil and 13 parts of clove essential oil uniformly, and then fill the mixed oil into a sealed bottle.

Preferred Embodiment 67

Mix and shake 30 parts of cinnamon essential oil, 20 parts of black pepper essential oil, 40 parts of juniper essential oil, 21 parts of ginger essential oil and 10 parts of clove essential oil uniformly, and then fill the mixed oil into a sealed bottle.

Preferred Embodiment 68

Mix and shake 48 parts of cinnamon essential oil, 38 parts of black pepper essential oil, 59 parts of juniper essential oil, 38 parts of ginger essential oil and 13 parts of clove essential oil uniformly, and then fill the mixed oil into a sealed bottle.

Preferred Embodiment 69

Mix and shake 32 parts of cinnamon essential oil, 32 parts of black pepper essential oil, 51 parts of juniper essential oil, 31 parts of ginger essential oil and 14 parts of clove essential oil uniformly, and then fill the mixed oil into a sealed bottle.

Preferred Embodiment 70

Mix and shake 21 parts of ginger essential oil, 21 parts of black pepper essential oil, 39 parts of juniper essential oil, 21 parts of jasmine essential oil and 2 parts of clove essential oil uniformly, and then fill the mixed oil into a sealed bottle.

Preferred Embodiment 71

Mix and shake 39 parts of ginger essential oil, 39 parts of black pepper essential oil, 58 parts of juniper essential oil, 37 parts of jasmine essential oil and 18 parts of clove essential oil uniformly, and then fill the mixed oil into a sealed bottle.

Preferred Embodiment 72

Mix and shake 31 parts of ginger essential oil, 31 parts of black pepper essential oil, 50 parts of juniper essential oil, 32 parts of jasmine essential oil and 13 parts of clove essential oil uniformly, and then fill the mixed oil into a sealed bottle.

Preferred Embodiment 73

Mix and shake 31 parts of cinnamon essential oil, 22 parts of ginger essential oil, 21 parts of black pepper essential oil, 43 parts of juniper essential oil, 22 parts of jasmine essential oil and 1 part of clove essential oil uniformly, and then fill the mixed oil into a sealed bottle.

Preferred Embodiment 74

Mix and shake 49 parts of cinnamon essential oil, 38 parts of ginger essential oil, 35 parts of black pepper essential oil, 59 parts of juniper essential oil, 38 parts of jasmine essential oil and 18 parts of clove essential oil uniformly, and then fill the mixed oil into a sealed bottle.

Preferred Embodiment 75

Mix and shake 42 parts of cinnamon essential oil, 32 parts of ginger essential oil, 33 parts of black pepper essential oil, 33 parts of juniper essential oil, 35 parts of jasmine essential oil and 10 parts of clove essential oil uniformly, and then fill the mixed oil into a sealed bottle.

Preferred Embodiment 76

Mix and shake 31 parts of cinnamon essential oil, 22 parts of black pepper essential oil, 43 parts of juniper essential oil and 31 parts of grape seed oil uniformly, and then fill the mixed oil into a sealed bottle.

Preferred Embodiment 77

Mix and shake 49 parts of cinnamon essential oil, 38 parts of black pepper essential oil, 57 parts of juniper essential oil and 59 parts of grape seed oil uniformly, and then fill the mixed oil into a sealed bottle.

Preferred Embodiment 78

Mix and shake 42 parts of cinnamon essential oil, 33 parts of black pepper essential oil, 52 parts of juniper essential oil and 42 parts of grape seed oil uniformly, and then fill the mixed oil into a sealed bottle.

Preferred Embodiment 79

Mix and shake 32 parts of cinnamon essential oil, 21 parts of black pepper essential oil, 21 parts of ginger essential oil and 31 parts of grape seed oil uniformly, and then fill the mixed oil into a sealed bottle.

Preferred Embodiment 80

Mix and shake 48 parts cinnamon essential oil, 37 parts of black pepper essential oil, 38 parts of ginger essential oil and 58 parts of grape seed oil uniformly, and then fill the mixed oil into a sealed bottle.

Preferred Embodiment 81

Mix and shake 45 parts of cinnamon essential oil, 35 parts of black pepper essential oil, 55 parts of ginger essential oil and 41 parts of grape seed oil uniformly, and then fill the mixed oil into a sealed bottle.

Preferred Embodiment 82

Mix and shake 31 parts of cinnamon essential oil, 32 parts of black pepper essential oil, 21 parts of jasmine essential oil and 31 parts of grape seed oil uniformly, and then fill the mixed oil into a sealed bottle.

Preferred Embodiment 83

Mix and shake 49 parts of cinnamon essential oil, 39 parts of black pepper essential oil, 38 parts of jasmine essential oil and 58 parts of grape seed oil uniformly, and then fill the mixed oil into a sealed bottle.

Preferred Embodiment 84

Mix and shake 42 parts of cinnamon essential oil, 29 parts of black pepper essential oil, 31 parts of jasmine essential oil and 42 parts of grape seed oil uniformly, and then fill the mixed oil into a sealed bottle.

Preferred Embodiment 85

Mix and shake 20 parts of black pepper essential oil, 43 parts of juniper essential oil, 22 parts of ginger essential oil and 31 parts of grape seed oil uniformly, and then fill the mixed oil into a sealed bottle.

Preferred Embodiment 86

Mix and shake 37 parts of black pepper essential oil, 58 parts of juniper essential oil, 37 parts of ginger essential oil and 57 parts of grape seed oil uniformly, and then fill the mixed oil into a sealed bottle.

Preferred Embodiment 87

Mix and shake 29 parts of black pepper essential oil, 51 parts of juniper essential oil, 31 parts of ginger essential oil and 42 parts of grape seed oil uniformly, and then fill the mixed oil into a sealed bottle.

Preferred Embodiment 88

Mix and shake 21 parts of a black pepper essential oil, 42 parts of a juniper essential oil, 22 parts of a jasmine essential oil, 3 parts of a clove essential oil and 59 parts of a grape seed oil uniformly, and then fill the mixed oil into a sealed bottle.

Preferred Embodiment 89

Mix and shake 35 parts of black pepper essential oil, 57 parts of juniper essential oil, 37 parts of jasmine essential oil, 20 parts of clove essential oil and 29 parts of grape seed oil uniformly, and then fill the mixed oil into a sealed bottle.

Preferred Embodiment 90

Mix and shake 31 parts of black pepper essential oil, 52 parts of juniper essential oil, 31 parts of jasmine essential oil, 11 parts of clove essential oil and 31 parts of grape seed oil uniformly, and then fill the mixed oil into a sealed bottle.

Preferred Embodiment 91

Mix and shake 22 parts of ginger essential oil, 42 parts of juniper essential oil, 22 parts of jasmine essential oil, 3 parts of clove essential oil and 33 parts of grape seed oil uniformly, and then fill the mixed oil into a sealed bottle.

Preferred Embodiment 92

Mix and shake 33 parts of ginger essential oil, 57 parts of juniper essential oil, 37 parts of jasmine essential oil, 18 parts of clove essential oil and 38 parts of grape seed oil uniformly, and then fill the mixed oil into a sealed bottle.

Preferred Embodiment 93

Mix and shake 32 parts of ginger essential oil, 52 parts of juniper essential oil, 31 parts of jasmine essential oil, 12 parts of clove essential oil and 39 parts of grape seed oil uniformly, and then fill the mixed oil into a sealed bottle.

Preferred Embodiment 94

Mix and shake 30 parts of cinnamon essential oil, 22 parts of black pepper essential oil, 40 parts of juniper essential oil, 21 parts of ginger essential oil, 2 parts of clove essential oil and 31 parts of grape seed oil uniformly, and then fill the mixed oil into a sealed bottle.

Preferred Embodiment 95

Mix and shake 48 parts of cinnamon essential oil, 38 parts of black pepper essential oil, 59 parts of juniper essential oil, 38 parts of ginger essential oil, 19 parts of clove essential oil and 32 parts of grape seed oil uniformly, and then fill the mixed oil into a sealed bottle.

Preferred Embodiment 96

Mix and shake 41 parts of cinnamon essential oil, 32 parts of black pepper essential oil, 51 parts of juniper essential oil, 31 parts of ginger essential oil, 13 parts of clove essential oil and 45 parts of grape seed oil uniformly, and then fill the mixed oil into a sealed bottle.

Preferred Embodiment 97

Mix and shake 30 parts of cinnamon essential oil, 22 parts of black pepper essential oil, 40 parts of juniper essential oil, 21 parts of ginger essential oil, 10 parts of clove essential oil and 32 parts of grape seed oil uniformly, and then fill the mixed oil into a sealed bottle.

Preferred Embodiment 98

Mix and shake 48 parts of cinnamon essential oil, 38 parts of black pepper essential oil, 59 parts of juniper essential oil, 38 parts of ginger essential oil, 13 parts of clove essential oil and 59 parts of grape seed oil uniformly, and then fill the mixed oil into a sealed bottle.

Preferred Embodiment 99

Mix and shake 30 parts of cinnamon essential oil, 30 parts of black pepper essential oil, 50 parts of juniper essential oil, 31 parts of ginger essential oil, 14 parts of clove essential oil and 33 parts of grape seed oil uniformly, and then fill the mixed oil into a sealed bottle.

Preferred Embodiment 100

Mix and shake 20 parts of ginger essential oil, 21 parts of black pepper essential oil, 40 parts of juniper essential oil, 20 parts of jasmine essential oil, 2 parts of clove essential oil and 32 parts of grape seed oil uniformly, and then fill the mixed oil into a sealed bottle.

Preferred Embodiment 101

Mix and shake 40 parts of ginger essential oil, 39 parts of black pepper essential oil, 58 parts of juniper essential oil, 37 parts of jasmine essential oil, 18 parts of clove essential oil and 58 parts of grape seed oil uniformly, and then fill the mixed oil into a sealed bottle.

Preferred Embodiment 102

Mix and shake 31 parts of ginger essential oil, 31 parts of black pepper essential oil, 50 parts of juniper essential oil, 32 parts of jasmine essential oil, 13 parts of clove essential oil and 42 parts of grape seed oil uniformly, and then fill the mixed oil into a sealed bottle.

Preferred Embodiment 103

Mix and shake 31 parts of cinnamon essential oil, 22 parts of ginger essential oil, 21 parts of black pepper essential oil, 43 parts of juniper essential oil, 22 parts of jasmine essential oil, 1 part of clove essential oil and 32 parts of grape seed oil uniformly, and then fill the mixed oil into a sealed bottle.

Preferred Embodiment 104

Mix and shake 49 parts of cinnamon essential oil, 38 parts of ginger essential oil, 35 parts of black pepper essential oil, 59 parts of juniper essential oil, 38 parts of jasmine essential oil, 18 parts of clove essential oil and 58 parts of grape seed oil uniformly, and then fill the mixed oil into a sealed bottle.

Preferred Embodiment 105

Mix and shake 42 parts of cinnamon essential oil, 32 parts of ginger essential oil, 33 parts of black pepper essential oil, 33 parts of juniper essential oil, 35 parts of jasmine essential oil, 10 parts of clove essential oil and 53 parts of grape seed oil uniformly, and then fill the mixed oil into a sealed bottle.

Preferred Embodiment 106

Mix and shake 40 parts of cinnamon essential oil, 32 parts of ginger essential oil, 33 parts of black pepper essential oil, 33 parts of juniper essential oil, 35 parts of jasmine essential oil, 10 parts of clove essential oil and 50 parts of grape seed oil uniformly, and then fill the mixed oil into a sealed bottle.

Method of Use: Dip a dry clean Q-tip into the mixed and shaken essential oil of the Preferred Embodiment 103, and smear the essential oil on affected areas. Apply the essential oil once or twice per day.

Test Population: Men with erectile dysfunction are randomly divided into seven groups, each having 10 persons.

The effect is observed continuously for three months after the essential oil is applied, and the observations show that each group of the erectile dysfunction patients has an improvement of a different level. The longer the time applied, the more significant is the effect.

The results observed are listed in the following table:

|  | Insignificant Effect | Effective | Significantly Improved | Efficient |
|---|---|---|---|---|
| Preferred Embodiment 1 | 1 person | 8 persons | 1 person | 90% |
| Preferred Embodiment 2 | 0 person | 6 persons | 4 persons | 100% |
| Preferred Embodiment 3 | 0 person | 9 persons | 1 person | 100% |
| Preferred Embodiment 4 | 4 persons | 5 persons | 1 person | 60% |
| Preferred Embodiment 5 | 3 persons | 7 persons | 0 person | 70% |
| Preferred Embodiment 6 | 2 persons | 6 persons | 2 persons | 80% |

-continued

|  | Insignificant Effect | Effective | Significantly Improved | Efficient |
|---|---|---|---|---|
| Preferred Embodiment 7 | 3 persons | 6 persons | 1 person | 80% |

Method of Use: Dip a dry clean Q-tip into the mixed and shaken essential oil of the Preferred Embodiment 35, and smear the essential oil on affected areas. Apply the essential oil once or twice per day.

Test Population: Men with erectile dysfunction are randomly divided into eight groups, each having 10 persons.

The effect is observed continuously for three months after the essential oil is applied, and the observations show that each group of the erectile dysfunction patients has an improvement of a different level. The longer the time applied, the more significant is the effect.

|  | Insignificant Effect | Effective | Significantly Improved | Efficient |
|---|---|---|---|---|
| Preferred Embodiment 1 | 2 persons | 7 persons | 1 person | 80% |
| Preferred Embodiment 2 | 3 persons | 6 persons | 1 person | 70% |
| Preferred Embodiment 3 | 0 person | 9 persons | 1 person | 100% |
| Preferred Embodiment 4 | 1 person | 5 persons | 4 persons | 90% |
| Preferred Embodiment 5 | 2 persons | 7 persons | 1 person | 80% |
| Preferred Embodiment 6 | 1 person | 6 persons | 3 persons | 90% |
| Preferred Embodiment 7 | 2 persons | 6 persons | 2 persons | 80% |
| Preferred Embodiment 8 | 3 persons | 4 persons | 3 persons | 70% |

Method of Use: Dip a dry clean Q-tip into the mixed and shaken essential oil of the Preferred Embodiment 55, and smear the essential oil on affected areas. Apply the essential oil once or twice per day.

Test Population: Men with erectile dysfunction are randomly divided into five groups, each having 10 persons.

The effect is observed continuously for three months after the essential oil is applied, and the observations show that each group of the erectile dysfunction patients has an improvement of a different level. The longer the time applied, the more significant is the effect.

The results observed are listed in the following table:

|  | Insignificant Effect | Effective | Significantly Improved | Efficient |
|---|---|---|---|---|
| Preferred Embodiment 1 | 1 person | 7 persons | 2 persons | 90% |
| Preferred Embodiment 2 | 1 person | 6 persons | 3 persons | 90% |
| Preferred Embodiment 3 | 3 persons | 6 persons | 1 person | 70% |
| Preferred Embodiment 4 | 3 persons | 5 persons | 2 persons | 70% |
| Preferred Embodiment 5 | 1 person | 7 persons | 2 persons | 80% |

What is claimed is:

1. A composition for treating erectile dysfunction in a human in need thereof consisting essentially of therapeutically effective amounts of cinnamon essential oil, black pepper essential oil, juniper essential oil, ginger essential oil, and jasmine essential oil.

\* \* \* \* \*